United States Patent [19]

Nakashima et al.

[11] Patent Number: 6,030,951
[45] Date of Patent: Feb. 29, 2000

[54] CHRYSOMYCIN DERIVATIVE COMPOUNDS AND USE AS ANTITUMOR AGENTS

[75] Inventors: Takashi Nakashima, Fujisawa; Tadashi Fujii, Tokyo; Kazuya Sakai, Yatsushiro; Tomohiro Sameshima, Fujisawa; Hiroyuki Kumagai, Chigasaki; Takeo Yoshioka, Ayase, all of Japan

[73] Assignee: Mercian Corporation, Japan

[21] Appl. No.: 09/308,710

[22] PCT Filed: Nov. 4, 1997

[86] PCT No.: PCT/JP97/04007

§ 371 Date: Jul. 8, 1999

§ 102(e) Date: Jul. 8, 1999

[87] PCT Pub. No.: WO98/22612

PCT Pub. Date: May 28, 1998

[30] Foreign Application Priority Data

Nov. 22, 1996 [JP] Japan .................................. 8-325834

[51] Int. Cl.[7] ............................. A61K 31/70; C07H 7/04
[52] U.S. Cl. ............................. 514/23; 514/27; 514/460; 536/1.11; 536/18.1; 536/18.2; 435/119
[58] Field of Search ................................ 514/23, 27, 460; 536/1.11, 18.1, 18.2; 435/119

[56] References Cited

U.S. PATENT DOCUMENTS 4,461,831  7/1984  Matson et al. .......................... 435/119
4,598,145  7/1986  Matson et al. .......................... 536/1.11

OTHER PUBLICATIONS

M. Jung et al., *Tetrahedron Letters*, 29(21), 2517–2520, (1988).

D. Hart et al., *Tetrahedron Letters*, 30(38), 5093–5096, (1989).

R. Misra et al., *J. Antibiotics*, 38(9), 1280–1283, (1985).

G. Carter et al., *J. Antibiotics*, 38(2), 242–248, (1985).

U. Weiss et al., *J. Antibiotics*, 35(9), 1194–1201, (1982).

T. Wei et al., *J. Antibiotics*, 35(4), 545–548, (1982).

*Primary Examiner*—Howard C. Lee
*Attorney, Agent, or Firm*—Wenderoth, Lind & Ponack, L.L.P.

[57] ABSTRACT

Disclosed are the novel C-glycoside compounds Mer-1020dA, Mer-1020dB, Mer-1020dC and Mer-1020dD which have a chromophore group in common with well-known chrysomycins A and B, but can be distinguished from the chrysomycins and the like in that the novel C-glycoside compounds have a sugar residue having a higher degree of oxidation, as well as the compound Mer-1020dE comprising only the chromophore thereof. Among these compounds, the C-glycoside compounds are antibiotics which have low toxicity and can strongly inhibit the growth of solid cancer cells in particular.

11 Claims, No Drawings

CHRYSOMYCIN DERIVATIVE COMPOUNDS AND USE AS ANTITUMOR AGENTS

This application is a 371 of PCT/JP97/04007 filed on Nov. 4, 1997.

TECHNICAL FIELD

This invention relates to C-glycosides produced by microorganisms, and an unglycosidated product thereof. These C-glycosides have a growth-inhibiting activity, for example, against tumor cells.

BACKGROUND ART

A large number of compounds have been proposed as antibiotics produced by microorganisms and having an antitumor activity. However, they generally have strong toxicity to normal cells or do not necessarily exhibit excellent effectiveness against solid cancers.

Chrysomycins and their related compounds are known as antibiotics having an antitumor activity and low toxicity (for example, U. Weiss et al., The Journal of Antibiotics, Vol. 35, 1982, 1194–1199). In the course of investigations on antibacteriophage active substances, chrysomycins were found as antibiotics produced by Streptomyces sp. A-419 and having an in vivo antitumor activity against P388 lymphocytic leukemia in mice.

However, there still remains a need for the provision of a compound having low toxicity and exhibiting remarkable effectiveness against solid cancers. Accordingly, an object of the present invention is to provide compounds which, as compared with well-known compounds, have low toxicity and more excellent efficacy against solid cancers in particular.

DISCLOSURE OF THE INVENTION

In order to accomplish the above object, the present inventors have carried on the screening of various microbial products while using high growth-inhibiting activity against solid cancer cells in particular, as an index. As a result, it has been found that a certain bacterial strain belonging to the genus Streptomyces produces compounds which show as low toxicity as the aforesaid chrysomycins and have more excellent growth-inhibiting activity against solid cancer cells than the chrysomycins. By isolating and examining these active substances, it has been confirmed that they are C-glycosides which have a chromophore residue in common with the chrysomycins and related antibiotics (i.e., gilvocarcins) but differ therefrom in sugar residue and which have not been described in the literature of the prior art.

Accordingly, the present invention provides the compound Mer-1020dA, Mer-1020dB, Mer-1020dC or Mer-1020dD represented by the following formula (I):

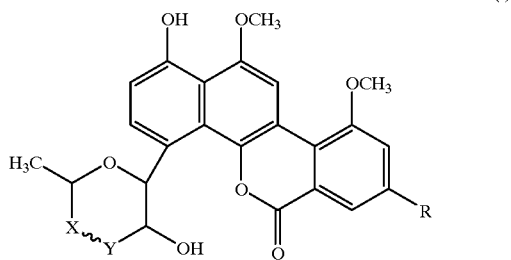

wherein the radicals R and X~Y are each of the following combinations of groups:

| Compound | R | X~Y |
|---|---|---|
| Mer-1020 dA | $CH_3$ | (structure with O=, OH, $CH_3$) |
| Mer-1020 dB | $CH_3$ | (structure with O, $CH_3$, OH) |
| Mer-1020 dC | (vinyl) | (structure with O, $CH_3$, OH) |
| Mer-1020 dD | (vinyl) | (structure with O=, OH, $CH_3$) |

Moreover, the present invention also provides a pharmaceutical preparation comprising, as an active ingredient, at least one compound selected from the group consisting of the aforesaid compounds Mer-1020dA, Mer-1020dB, Mer-1020dC and Mer-1020dD, and a physiologically acceptable additive.

Moreover, the present invention also provides the use of at least one of the aforesaid compounds in the making of a pharmaceutical preparation, and a method for the treatment of a tumor which comprises administering at least one of the aforesaid compounds, optionally together with a physiologically acceptable additive, to a mammal, particularly a human being, having a tumor.

Moreover, the present invention also provides the compound Mer-1020dE which is represented by the following formula (II) and can be used as a precursor for the biosynthesis or chemical synthesis of the aforesaid compounds in particular:

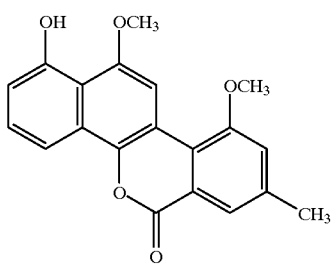

(II)

Furthermore, the present invention also provides a fermentation process for preparing any of the compounds represented by the above formulae (I) and (II).

DETAILED DESCRIPTION OF THE INVENTION

For convenience' sake, the present inventors named the compounds of the present invention as described above. More specifically, these compounds can be specified by the following respective structural formulae in which various groups are united together.

Compound Mer-1020dA:

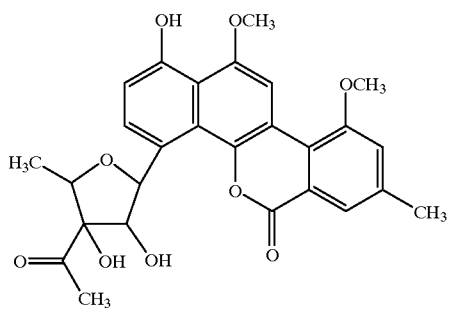

(I-a)

Compound Mer-1020dB:

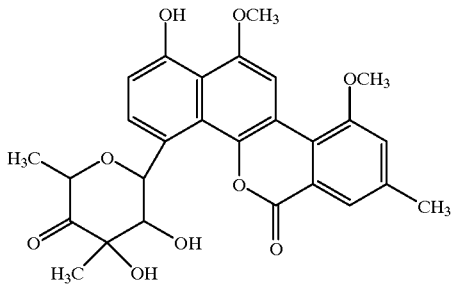

(I-b)

Compound Mer-1020dC:

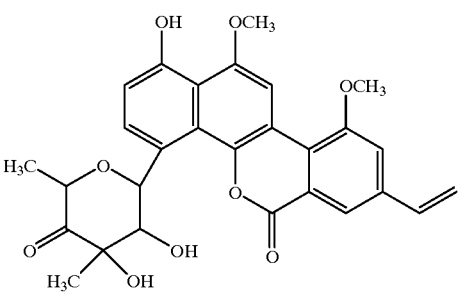

(I-c)

Compound Mer-1020dD:

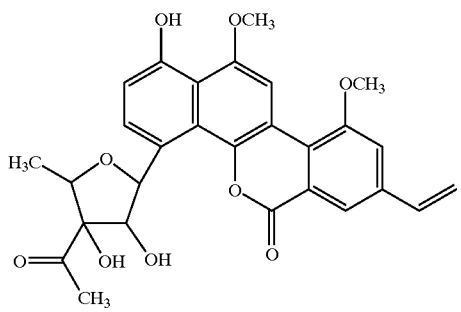

(I-d)

As may be understood from the above structural formulae, the compound Mer-1020dB corresponds to a compound in which the hydroxyl group at the 4-position of the pyranose sugar residue of chrysomycin B is oxidized to a carbonyl group, and the compound Mer-1020dC corresponds to a compound in which the hydroxyl group at the 4-position of the pyranose sugar residue of chrysomycin A is oxidized to a carbonyl group.

Each of the aforesaid compounds in accordance with the present invention has a more excellent growth-inhibiting activity than chrysomycins A and B, with respect to at least one type of cultured solid cancer cells. Among others, the compound Mer-1020dA has a significantly excellent growth-inhibiting activity against all types of cultured solid cancers used for testing purposes, and is hence a useful compound.

The aforesaid novel C-glycosides can be prepared by the culture of any bacterial strain belonging to the genus *Streptomyces* and capable of producing them. One specific example thereof is the bacterial strain which was isolated from soil collected on the banks of the Hikiji River in Fujisawa City by the present inventors and named Mer-1020. This strain was identified as *Streptomyces* sp. because it has diaminopimellic acid in LL form and forms well-growing aerial hyphae. This strain was deposited as *Streptomyces* sp. Mer-1020 with the National Institute of Bioscience and Human Technology, the Agency of Industrial Science and Technology, and assigned the accession number FERM P-15888 on Sep. 27, 1996. Thereafter, the aforesaid strain was transferred to the international deposition department of the aforesaid institute under the provisions of the Budapest Treaty on the International Recognition of the Deposit of Microorganisms for the Purposes of Patent Procedure, and is maintained as FERM BP-5984.

As will be more fully described later, the Mer-1020 strain can produce, in addition to the aforesaid C-glycosides of the present invention, a compound which comprises only the chromophore thereof (i.e., does not have a sugar residue) as represented by the following formula and which was named Mer-1020dE.

Compound Mer-1020dE:

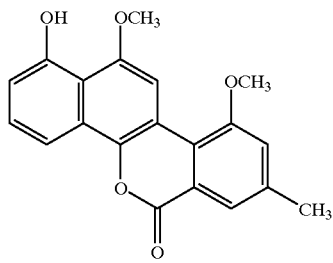

This compound Mer-1020dE is also a novel compound which has not been described in the literature of the prior art. Although the growth-inhibiting activity of the compound Mer-1020dE itself against the aforesaid various types of tumor cells is lower as compared with chrysomycins, Mer-1020dE is a compound which can be used not only as a precursor for the biosynthesis or chemical synthesis of the aforesaid compounds Mer-1020dA to D, but also as an intermediate for the synthesis of other compounds. Accordingly, the compound Mer-1020dE is also an embodiment of the present invention.

The aforesaid compounds Mer-1020dA to E may be prepared by a preparation process which is provided according to another aspect of the present invention as described above, i.e., a process for the preparation of the aforesaid compounds which comprises the steps of culturing a bacterial strain belonging to the genus *Streptomyces* and capable of producing at least one of the compounds Mer-1020dA to E, in a culture medium; and harvesting at least one compound selected from the group consisting of the compounds Mer-1020dA, Mer-1020dB, Mer-1020dC, Mer-1020dD and Mer-1020dE, from the resulting culture.

Specifically, the aforesaid Mer-1020 strain (FERM BP-5984) is cultured in a culture medium so as to cause the compounds Mer-1020dA to E to be produced and accumulated. Then, these compounds may be harvested, either alone or as a mixture, from the resulting culture.

Similarly to the per se known culture method employed for the production of antibiotics by actinomyces, a liquid culture method, particularly a submerged culture method, under aerobic conditions is suitable for this purpose.

Any nutrient sources may be used for the aforesaid culture, provided that the Mer-1020 strain can utilize them. In practice, there may be used any of the carbon sources, nitrogen sources and other nutrients which have conventionally been used for the culture of actinomyces. For example, as carbon sources, glucose, galactose, maltose, dextrin, starch, starch syrup, soybean oil and the like may be used alone or in admixture. As nitrogen sources, ammonium chloride, urea, ammonium sulfate, ammonium nitrate, sodium nitrate, peptone, meat extract, yeast extract, dry yeast, corn steep liquor, soybean meal, oatmeal, casamino acid, Bacto Soyton (DIFCO Corp.) and the like may be used alone or in admixture. Moreover, if necessary, inorganic salts such as sodium chloride, magnesium sulfate, calcium carbonate, phosphoric acid salts and metallic salts may be added, and other organic substances which promote the growth of this strain or the production of Mer-1020dA to E, such as vitamins and amino acids, may also be added. Furthermore, antifoaming agents [e.g., Adekanol (manufactured by Asahi Denka Kogyo K.K.)], silicones and the like may be added as required.

The temperature suitable for the aforesaid culture is in the range of 20 to 30° C., and the pH of the culture medium is desirably in the vicinity of neutrality. Usually, when a liquid culture is carried out for 3 to 5 days, Mer-1020dA to E are accumulated in the culture medium. As soon as the amount of the compounds formed in the culture medium has reached a maximum, the incubation is stopped. Then, the compounds Mer-1020dA to E, which are the desired substances, may be isolated and purified from the bacterial cells and the culture medium obtained by filtration.

In order to isolate and purify the compounds Mer-1020dA to E from the bacterial cells and culture medium thus obtained, there may be used any suitable combination of techniques such as silica gel column chromatography and high-performance liquid chromatography.

Among the compounds Mer-1020dA to E thus obtained, Mer-1020dA, Mer-1020dB, Mer-1020dC and Mer-1020dD exhibit remarkable effectiveness against cells derived from tumors, particularly solid cancers (e.g., colic cancer, mammary cancer, pulmonary cancer and gastric cancer), of mammals and, in particular, human beings. Consequently, they can be used as active ingredients for pharmaceutical preparations.

These pharmaceutical preparations may be made by using the compounds of the present invention in combination with physiologically acceptable additives which are commonly used in the technical field of pharmaceutics. More specifically, the aforesaid additives include all of the solid, semisolid or liquid diluents, fillers and compounding aids used in this technical field. Accordingly, the pharmaceutical preparations of the present invention may have any of various dosage forms such as tablets, capsules, granules, suppositories, solutions, suspensions and emulsions.

Tablets, capsules and granules contain one or more of the compounds of the present invention (which may hereinafter referred to as active ingredients) together with additives. Such additives include fillers and extenders (e.g., starch, lactose, glucose, mannitol and silica), binders (e.g., alginates, carboxymethyl-cellulose, gelatin and polyvinyl pyrrolidone), humectants (e.g., glycerol), disintegrators (e.g., agar, calcium carbonate and sodium bicarbonate), dissolution retarders (e.g., paraffin), absorption accelerators (e.g., quaternary ammonium compounds), wetting agents (e.g., cetyl alcohol and glycerol monostearate), adsorbents (e.g., kaolin and bentonite) and lubricants (e.g., talc, calcium stearate, magnesium stearate and solid polyethylene glycol). The aforesaid tablets and granules may be sustained-release preparations which permit the active ingredient to be released at a controlled rate in the living body. Moreover, such sustained-release preparations may be adapted for embedment in the affected part or its neighborhood. Usually, this may be done by using a polymer matrix or wax.

Suppositories may contain, in addition to the active ingredient, commonly used water-soluble or water-insoluble additives such as polyethylene glycol, fats (e.g., cacao butter), higher esters (e.g., esters derived from a $C_{14}$-alcohol and a $C_{16}$-fatty acid), and mixtures thereof.

Solutions and emulsions may contain, in addition to the active ingredient, commonly used additives including, for example, solvents, solubilizers and emulsifiers, such as water, ethyl alcohol, isopropyl alcohol, ethyl carbonate, ethyl acetate, benzyl alcohol, propylene glycol, 1,3-butylene glycol, dimethylformamide, oils (in particular, cottonseed oil, peanut oil, corn oil, olive oil, castor oil and sesame oil), glycerol, polyethylene glycol, sorbitan fatty acid esters, and mixtures thereof.

Suspensions may contain, in addition to the active ingredient, commonly used additives such as liquid diluents (e.g., water, ethyl alcohol and propylene glycol), suspending agents (e.g., ethoxylated isostearyl alcohol, polyoxyethylene sorbitol and sorbitan esters), microcrystalline cellulose, aluminum metahydroxide, bentonite, agar, tragacanth and mixtures thereof.

Where the aforesaid solutions and emulsions are used for purposes of parenteral administration, their osmotic pressure may further be regulated so as to be isotonic.

Moreover, pharmaceutical preparations in any of the aforesaid dosage forms may also contain other additives such as preservatives.

Where the compounds of the present invention are formed into pharmaceutical preparations as described above, these compounds (active ingredients) may comprise about 0.1 to 99.5% by weight, preferably about 0.5 to 95% by weight, of the total weight of the pharmaceutical preparation.

The optimum dosage of the active ingredients may vary according to the type and condition of the individual being treated, such as, in the case of human subjects, sex (male or female), age (child, adult or aged), and severity of disease (mild or serious). Accordingly, their dosage should be determined by a medical specialist. However, in the case of parenteral administration, the active ingredients are generally administered in a daily dose of about 0.5 to about 500 mg, preferably 10 to 100 mg, per kg of body weight which may be divided into several doses, if necessary.

The present invention is further illustrated by the following specific examples. These examples are given merely to facilitate the understanding of the present invention.

EXAMPLE 1

Preparation of the compounds Mer-1020dA to E

Three 250 ml Erlenmeyer flasks each containing 25 ml of a seed culture medium (2% potato starch, 2% glucose, 2% Esusan Meat (Ajinomoto Co., Inc.), 0.5% yeast extract, 0.25% sodium chloride, 0.32% calcium carbonate, 0.0005% magnesium sulfate, 0.0005% manganese chloride, 0.0005% zinc sulfate, pH 7.4) were inoculated with a loopful of the Mer-1020 strain which had been grown on a slant medium (a potato-dextrose agar medium), and incubated at 28° C. for 3 days on a gyratory shaker (180 rpm) to obtain a seed culture. Then, fifty 500 ml Erlenmeyer flasks each containing 100 ml of a production medium (2% potato starch, 2% glucose, 2% Esusan Meat, 0.5% yeast extract, 0.25% sodium chloride, 0.32% calcium carbonate, 0.0005% magnesium sulfate, 0.0005% manganese chloride, 0.0005% zinc sulfate, pH 7.4) were inoculated with 75 ml of the above seed culture, and incubated at 28° C. for 96 hours on a gyratory shaker.

After completion of the incubation, the resulting culture (about 5 L) was separated into bacterial cells and filtrate by filtration. Thus, about 4 L of culture filtrate was obtained. Without adjusting its pH, this culture filtrate was extracted twice with 2.5 L of ethyl acetate. The extract was concentrated to dryness under reduced pressure to obtain 4.6 g of an ethyl acetate extract. On the other hand, the bacterial cells were extracted with 5 L of methanol, and the extract was concentrated to 500 mL under reduced pressure. The resulting concentrate was diluted with 2 L of water and then extracted with 2.5 L of ethyl acetate. The extract was concentrated to dryness under reduced pressure to obtain 4.9 g of a bacterial cell extract. 3.92 g of the bacterial cell extract was subjected to silica gel column chromatography [Kieselguhr 60 manufactured by Merck & Co., Inc., 2.5Ø× 40 cm, eluted with toluene/acetone (5:1)], and the resulting fractions containing the compounds Mer-1020dA, Mer-1020dB, Mer-1020dC and Mer-1020dD were concentrated to dryness to obtain 477 mg of a fraction containing the compounds Mer-1020dA to dD. Moreover, there was also obtained 129 mg of a fraction containing the compound Mer-1020dE. 477 mg of the fraction containing the compounds Mer-1020dA to dD was purified by use of an ODS column [Shim-Pack PREP ODS (H) KIT (manufactured by Shimadzu Corp., 20Ø×250 mm]. Using a 55% aqueous solution of acetonitrile as the mobile phase, high-performance liquid chromatography was carried out at a feed rate of 7 ml per minutes. As a result, fractions containing the compounds Mer-1020dA, Mer-1020dB and Mer-1020dC/Mer-1020dD were obtained in amounts of 94 mg, 167 mg and 120 mg, respectively.

Each fraction was further purified by use of an ODS column (Shim-Pack PREP ODS (H) KIT, 20Ø×250 mm). Using a 50% aqueous solution of acetonitrile as the mobile phase, high-performance liquid chromatography was carried out at a feed rate of 7 ml per minutes. As a result, the compounds Mer-1020dA, Mer-1020dB, Mer-1020dC and Mer-1020dD were obtained in yields of 29 mg, 71 mg, 24 mg and 19 mg, respectively. 10 mg of the fraction containing the compound Mer-1020dE was purified by use of an ODS column (Shim-Pack PREP ODS (H) KIT, 20Ø×250 mm). Using a 50% aqueous solution of acetonitrile as the mobile phase, high-performance liquid chromatography was carried out at a feed rate of 7 ml per minutes. As a result, the compounds Mer-1020dE was obtained in a yield of 3 mg.

Physicochemical properties of the compounds Mer-1020dA, Mer-1020dB, Mer-1020dC, Mer-1020dD and Mer-1020dE are shown below.

1020dA (1) Color and form: Yellow powder.

(2) Distinction between neutrality, acidity and basicity: Neutral.

(3) Solubility: Soluble in organic solvents such as chloroform, acetone and methanol, but insoluble in water.

(4) Rf value in thin-layer chromatography: 0.56 when Silica Gel F254 (manufactured by Merck & Co., Inc.) was used in combination with a developing solvent comprising toluene-acetone (2:1).

(5) Molecular weight: 494.

(6) Molecular formula: $C_{27}H_{26}O_9$.

(7) Ultraviolet absorption spectrum: $\lambda$ MeOH$_{max}$ (nm); 244($\epsilon$ 57800), 267(sh), 275($\epsilon$ 40700), 308($\epsilon$ 13400), 319($\epsilon$ 13500), 383($\epsilon$ 12500).

(8) Infrared absorption spectrum (KBr method): The wavenumbers (cm$^{-1}$) of chief absorption bands are as follows. 3370, 1698, 1618, 1451, 1372, 1339, 1298, 1250, 1196, 1134, 1117.

(9) $^1$H-NMR spectrum: $^1$H-NMR (400 MHz, CDCl$_3$) δ (ppm); 1.44(3 H, d, J=6.6), 2.32(3 H, s), 2.51(3 H, s), 4.07(3 H, s), 4.10(3 H, s), 4.20(1 H, q, J=6.6), 4.34(1 H, s), 6.00(1 H, d, J=4.4), 7.08(1 H, d, J=8.8), 7.16(1 H, s), 7.85(1 H, s), 8.10(1 H, d, J=8.8), 8.36(1 H, s), 9.70(1 H, s).

(10) $^{13}$C-NMR spectrum: $^{13}$C-NMR (400 MHz, CDCl$_3$) δ (ppm); 14.96(q), 21.69(q), 27.87(q), 56.27(q), 56.34(q), 79.54(d), 81.92(d), 85.35(d), 85.53(s), 101.76(d), 112.81(d), 113.66(s), 115.33(s), 118.82(d), 121.16(s), 122.07(s), 122.25(d), 124.68(s), 125.73(s), 130.46(s), 140.40(s), 141.59(s), 152.67(s), 153.91(s), 157.07(s), 162.73(s), 210.03(s).

1020dB (1) Color and form: Yellow powder.

(2) Distinction between neutrality, acidity and basicity: Neutral.

(3) Solubility: Soluble in organic acids such as chloroform, acetone and methanol, but insoluble in water.

(4) Rf value in thin-layer chromatography: 0.56 when Silica Gel F254 (manufactured by Merck & Co., Inc.) is used in combination with a developing solvent comprising toluene-acetone (2:1).

(5) Molecular weight: 494.

(6) Molecular formula: $C_{27}H_{26}O_9$.

(7) Ultraviolet absorption spectrum: λ MeOH$_{max}$ (nm); 245 (ε 39900), 267(sh), 275(29100), 307(ε 9,500), 319(ε 9,600), 383(ε 8,800).

(8) Infrared absorption spectrum (KBr method): The wavenumbers (cm$^{-1}$) of chief absorption bands are as follows. 3374, 1742, 1698, 1616, 1449, 1372, 1341, 1307, 1250, 1184, 1132.

(9) $^1$H-NMR spectrum: $^1$H-NMR (400 MHz, CDCl$_3$)δ (ppm); 1.39(3 H, s), 1.55(3 H, d, J=6.6), 2.53(3 H, s), 4.10(3 H, s), 4.15(3 H, s), 4.20(1 H, s), 4.73(1 H, q, J=6.6), 6.14(1 H, s), 7.06(1 H, d, J=8.8), 7.23(1 H, s), 7.89(1 H, s), 8.18(1 H, d, J=8.1), 8.50(1 H, s), 9.80(1 H, s).

(10) $^{13}$C-NMR spectrum: $^{13}$C-NMR (400 MHz, CDCl$_3$) δ (ppm); 16.52(q), 20.50(q), 21.69(q), 56.39(q), 56.45(q), 77.14(d), 77.32(d), 79.54(d), 81.84(d), 102.43(d), 112.55(d), 114.22(s), 115.77(s), 119.08(d), 121.03(s), 121.92(s), 122.49(d), 123.84(s), 126.24(s), 128.72(d), 140.89(s), 141.37(s), 152.71(s), 154.11(s), 157.18(s), 162.79(s), 213.26(s).

1020dC (1) Color and form: Yellow powder.

(2) Distinction between neutrality, acidity and basicity: Neutral.

(3) Solubility: Soluble in organic acids such as chloroform, acetone and methanol, but insoluble in water.

(4) Rf value in thin-layer chromatography: 0.56 when Silica Gel F254 (manufactured by Merck & Co., Inc.) is used in combination with a developing solvent omprising toluene-acetone (2:1).

(5) Molecular weight: 506.

(6) Molecular formula: $C_{28}H_{26}O_9$.

(7) Ultraviolet absorption spectrum: λ MeOH$_{max}$ (nm); 248(ε 30800), 277(sh), 287(ε 3000), 394(ε 11200).

(8) Infrared absorption spectrum (KBr method): The wavenumbers (cm$^{-1}$) of chief absorption bands are as follows. 3378, 1738, 1699, 1622, 1451, 1372, 1339, 1294, 1248, 1132, 1113.

(9) $^1$H-NMR spectrum: $^1$H-NMR (400 MHz, CDCl$_3$) δ (ppm); 1.39(3 H, s), 1.55(3 H, d, J=6.6), 4.16(3 H, s), 4.17(3 H, s), 4.20(1 H, s), 4.73(1 H, q, J=6.6), 5.51 (1 H, d, J=17.6), 5.98(1 H, d, J=11.0), 6.14(1 H, s), 6.82(1 H, dd, J=17.6, 11.0), 7.08(1 H, d, J=8.8), 7.44(1 H, s), 8.10(1 H, s), 8.18(1 H, d, J=8.8), 8.51(1 H, s), 9.80(1 H, s).

(10) $^{13}$C-NMR spectrum: $^{13}$C-NMR (400 MHz, CDCl$_3$) δ (ppm); 16.50(q), 20.49(q), 56.34(q) , 56.46(q), 77.13(d), 77.32(d), 79.57(d), 81.69(d), 102.21(d), 112.81(d), 113.99 (d), 114.83(s), 115.90(s), 117.22(t), 120.23(d), 121.34(s), 123.58(s), 123.75(s), 126.29(s), 128.82(d), 134.98(s), 139.39(d), 141.65(s), 152.90(s), 154.11(s), 157.45(s), 162.61(s), 210.13(s).

1020dD (1) Color and form: Yellow powder.

(2) Distinction between neutrality, acidity and basicity: Neutral.

(3) Solubility: Soluble in organic acids such as chloroform, acetone and methanol, but insoluble in water.

(4) Rf value in thin-layer chromatography: 0.56 when Silica Gel F254 (manufactured by Merck & Co., Inc.) is used in combination with a developing solvent comprising toluene-acetone (2:1).

(5) Molecular weight: 506.

(6) Molecular formula: $C_{28}H_{26}O_9$.

(7) Ultraviolet absorption spectrum: λ MeOH$_{max}$ (nm); 206(ε 17900), 246(ε 26900), 278(ε 22100), 287(sh), 391(ε 8900).

(8) Infrared absorption spectrum (KBr method): The wavenumbers (cm$^{-1}$) of chief absorption bands are as follows. 3378, 1709, 1622, 1587, 1453, 1373, 1288, 1250, 1195, 1132.

(9) $^1$H-NMR spectrum: $^1$H-NMR (400 MHz, CDCl$_3$) δ (ppm); 1.44(3 H, d, J=6.6), 2.33(3 H, s), 4.11(3 H, s), 4.12(3 H, s), 4.21(1 H, q, J=6.6), 4.35(1 H, d, J=2.9), 5.48(1 H, d, J=11.0), 5.95(1 H, d, J=17.6), 6.02(1 H, d, J=4.4), 6.81 (1 H, dd, J=17.6,11.0), 7.09(1 H, d, J=8.8), 7.39(1 H, d, J=2.2), 8.06(1 H, d, J=1.5), 8.10(1 H, d, J=8.1), 8.51(1 H, s), 9.71(1 H, s).

(10) $^{13}$C-NMR spectrum: $^{13}$C-NMR (400 MHz, CDCl$_3$) δ (ppm); 15.39(q), 28.12(q), 56.55(q), 56.69(q), 79.93(d), 82.33(d), 85.46(d), 85.93(s), 101.91(d), 113.40(d), 113.79 (d), 114.93(d), 115.81(s), 117.26(t), 120.35(d), 121.84(s), 124.10(s) 124.53(s), 126.14(s), 130.78(d), 135.46(s), 139.37 (d), 142.22(s), 152.97(s), 154.31(s), 157.69(s), 162.84(s), 210.32(s).

1020dE (1) Color and form: Yellow powder.

(2) Distinction between neutrality, acidity and basicity: Neutral.

(3) Solubility: Soluble in organic acids such as chloroform, acetone and methanol, but insoluble in water.

(4) Rf value in thin-layer chromatography: 0.56 when Silica Gel F254 (manufactured by Merck & Co., Inc.) is used in combination with a developing solvent comprising toluene-acetone (2:1).

(5) Molecular weight: 336.

(6) Molecular formula: $C_{20}H_{16}O_5$.

(7) Ultraviolet absorption spectrum: λ MeOH$_{max}$ (nm); 243(ε 30400), 264(ε 17900), 273(ε 21800), 302(ε 8900), 341(ε 5100), 381(ε 7300).

(8) Infrared absorption spectrum (KBr method): The wavenumbers (cm$^{-1}$) of chief absorption bands are as follows. 3374, 1720, 1387, 1361, 1128, 1061.

(9) $^1$H-NMR spectrum: $^1$H-NMR (400 MHz, CDCl$_3$) δ (ppm); 2.50(3 H, s), 4.07(3 H, s), 4.12(3 H, s), 7.00(1 H, d, J=6.6), 7.13(1 H, s), 7.49(1 H, t, J=8.1), 7.94(1 H, s), 8.07(1 H, d, J=7.3), 8.33(1 H, s) , 9.36(1 H, s).

(10) $^{13}$C-NMR spectrum: $^{13}$C-NMR (400 MHz, CDCl$_3$) δ (ppm); 21.63(q), 56.04(q), 56.22(q), 101.77(d), 112.44(d), 112.94(s), 113.42(d), 114.64(s), 118.12(d), 121.79(s), 122.86(s), 123.07 (d), 126.20(s), 128.44(d), 139.89(s), 151.82(s), 154.16(s), 156.99(s), 161.27(s).

EXAMPLE 2

Tests for the Inhibition of the Growth of Various Human Cancer Cells

Using various human cancer cells, the concentrations of test compounds which inhibits the growth of cancer cells by 50% were determined. Specifically, each of K562 (leukemic cell), HT29 (colic cancer), HT1080 (reticulogranuloma cell), MCF7 (mammary cancer cell), PC6 (pulmonary cancer cell) and MKN28 (gastric cancer cell) was added to a 96-well microtiter/plate at a density of $2–5\times10^3$ cells per well, and RPM11640 medium (phenol red-free) containing 10% FBS, together with a test compound, was added thereto. Then, this plate was incubated at 37° C. for 3 days in an atmosphere of air containing 5% $CO_2$. Thereafter, 10 μl of WST-1 reagent [0.065% 2-(4-iodophenyl)-3-(4-nitrophenyl)-5-(2,4-disulfonyl)-2H-tetrazolium monosodium salt, 0.007% 1-methoxy-5-methylphenazium methylsulfate] was added to each well, and the plate was further incubated for 3 hours. Then, the absorbance of each well at 450 nm (with a reference wavelength of 650 nm) was measured with a plate reader. The results thus obtained are shown in Table I.

TABLE I

Cancer Cell Growth-Inhibiting Activity of 1020dA to E against Various Human Cancer Cells
$IC_{50}$ value (μg/ml)

| Compound | K562 | HT29 | MCF7 | PC6 | MKN28 |
|---|---|---|---|---|---|
| Mer-1020dA | 0.36 | 0.075 | 0.032 | 0.064 | 0.017 |
| Mer-1020dB | 0.28 | 0.35 | 0.35 | 0.11 | 0.35 |
| Mer-1020dC | 0.11 | 0.10 | 0.42 | 0.03 | 0.32 |
| Mer-1020dD | 0.21 | 0.15 | 0.60 | 2.5 | 1.0 |
| Mer-1020dE | 8.1 | 19 | 17 | 34 | 11 |
| Chrysomycin A (for comparison) | 0.106 | 0.84 | 0.53 | 0.335 | 0.144 |
| Chrysomycin B (for comparison) | 1.76 | 2.63 | 2.58 | 3.5 | 2.65 |

It can be seen from Table I that, as compared with chrysomycin A, the compounds Mer-1020dA to D show little significant difference in growth-inhibiting activity against leukemic cells, but are significantly more excellent in growth-inhibiting activity against at least one type of cultured cells falling under the category of solid cancer cells.

Exploitability in Industry

The present invention provides novel compounds which, as compared with chrysomycins known to have very low toxicity, for example, when administered intraperitoneally to mice, have almost equal toxicity, but can significantly strongly inhibit the growth of cultured solid cancer cells in particular. Accordingly, the present invention can be utilized in the fields of pharmaceutics and medicine.

We claim:

1. The compound Mer-1020dA, Mer-1020dB, Mer-1020dC or Mer-1020dD represented by the following formula (I):

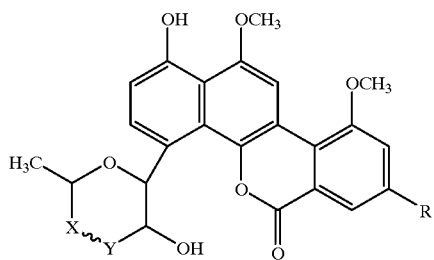

wherein the radicals R and X~Y are each of the following combinations of groups:

| Compound | R | X~Y |
|---|---|---|
| Mer-1020 dA | $CH_3$ | (structure with $O=$, $OH$, $CH_3$) |
| Mer-1020 dB | $CH_3$ | (structure with $O$, $CH_3$, $OH$) |
| Mer-1020 dC | (vinyl) | (structure with $O=$, $CH_3$, $OH$) |
| Mer-1020 dD | (vinyl) | (structure with $O=$, $OH$, $CH_3$) |

2. The compound Mer-1020dA represented by the formula (I-a):

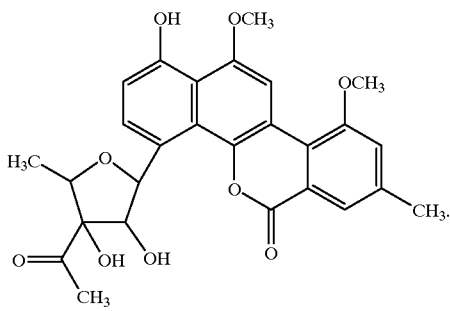

3. The compound Mer-1020dB represented by the formula (I-b):

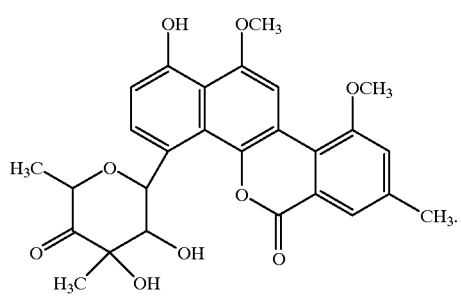
(I-b)

4. The compound Mer-1020dC represented by the formula (I-c):

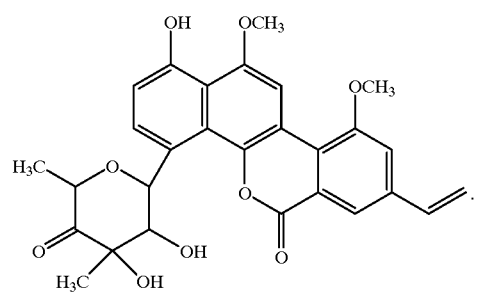
(I-c)

5. The compound Mer-1020dD represented by the formula (I-d):

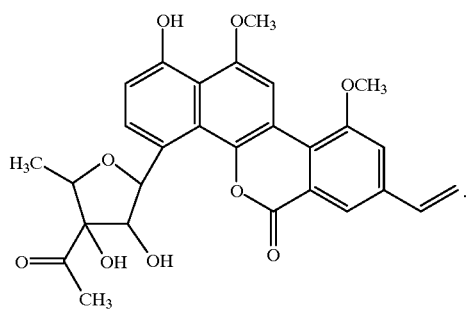
(I-d)

6. A process for the preparation of at least one compound selected from the group consisting of the compounds Mer-1020dA, Mer-1020dB, Mer-1020dC, Mer-1020dD and Mer-1020dE as claimed in any of claims 1 to 5, which comprises the steps of culturing a bacterial strain belonging to the genus *Streptomyces* and capable of producing any of said compounds, in a nutrient medium; and harvesting at least one compound selected from the group consisting of the compounds Mer-1020dA, Mer-1020dB, Mer-1020dC, Mer-1020dD and Mer-1020dE, from the resulting culture.

7. A pharmaceutical preparation comprising, as an active ingredient, at least one compound selected from the group consisting of the compounds Mer-1020dA, Mer-1020dB, Mer-1020dC and Mer-1020dD represented by the following formula (I), and a physiologically acceptable additive,

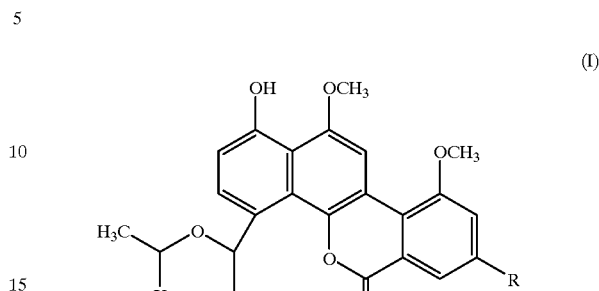
(I)

wherein the radicals R and X~Y are each of the following combinations of groups:

| Compound | R | X~Y |
|---|---|---|
| Mer-1020 dA | $CH_3$ | (structure with C=O, OH, $CH_3$) |
| Mer-1020 dB | $CH_3$ | (structure with O, $CH_3$, OH) |
| Mer-1020 dC | vinyl | (structure with O, $CH_3$, OH) |
| Mer-1020 dD | vinyl | (structure with C=O, OH, $CH_3$) |

8. A pharmaceutical preparation as claimed in claim 7 wherein the active ingredient is contained in a sufficient amount to exhibit an antitumor activity.

9. A pharmaceutical preparation as claimed in claim 7 wherein the active ingredient is contained in a sufficient amount to treat a solid cancer.

10. A method of making a pharmaceutical preparation which comprises employing at least one compound selected from the group consisting of the compounds Mer-1020dA, Mer-1020dB, Mer-1020dC and Mer-1020dD represented by the following formula (I), in the making of a pharmaceutical preparation:

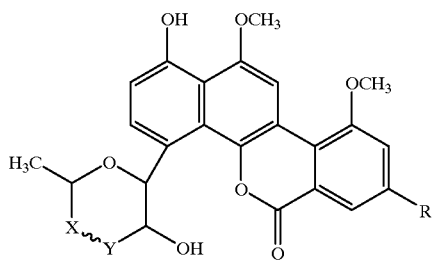

wherein the radicals R and X~Y are each of the following combinations of groups:

| Compound | R | X~Y |
|---|---|---|
| Mer-1020 dA | CH₃ | (structure) |
| Mer-1020 dB | CH₃ | (structure) |
| Mer-1020 dC | (vinyl) | (structure) |
| Mer-1020 dD | (vinyl) | (structure) |

11. A method for the treatment of a mammal having a tumor which comprises administering at least one compound selected from the group consisting of the compounds Mer-1020dA, Mer-1020dB, Mer-1020dC and Mer-1020dD represented by the following formula (I), in a sufficient amount to treat tumors and optionally in combination with a physiologically acceptable additive, to a mammal requiring the treatment of a tumor,

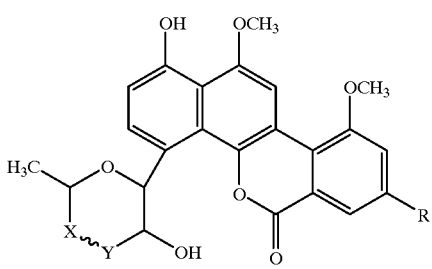

wherein the radicals R and X~Y are each of the following combinations of groups:

| Compound | R | X~Y |
|---|---|---|
| Mer-1020 dA | CH₃ | (structure) |
| Mer-1020 dB | CH₃ | (structure) |
| Mer-1020 dC | (vinyl) | (structure) |
| Mer-1020 dD | (vinyl) | (structure) |

* * * * *